(12) United States Patent
Hirofumi

(10) Patent No.: US 6,916,859 B2
(45) Date of Patent: *Jul. 12, 2005

(54) ANTI-MICROBIAL TOOL GRIP

(75) Inventor: Konishi Hirofumi, Osaka (JP)

(73) Assignee: Hakko Corporation (JP)

(*) Notice: Subject to any disclaimer, the term of this patent is extended or adjusted under 35 U.S.C. 154(b) by 0 days.

This patent is subject to a terminal disclaimer.

(21) Appl. No.: 10/348,684

(22) Filed: Jan. 22, 2003

(65) Prior Publication Data
US 2005/0101691 A1 May 12, 2005

(51) Int. Cl.$^7$ .............................. C08K 3/34; C08K 3/22; C08K 3/08; A01N 59/16
(52) U.S. Cl. ......................... 523/122; 523/103; 16/422; 16/426; 424/618
(58) Field of Search ......................... 424/618; 523/103, 523/122; 16/422, 426; 264/238

(56) References Cited

U.S. PATENT DOCUMENTS

| | | | | |
|---|---|---|---|---|
| 3,689,449 A | * | 9/1972 | Yeager et al. ................ 523/122 |
| 4,034,079 A | * | 7/1977 | Schoonman ................ 424/659 |
| 4,603,152 A | * | 7/1986 | Laurin et al. ................ 604/265 |
| 5,047,448 A | * | 9/1991 | Tanaka et al. ................ 523/122 |
| 5,281,288 A | * | 1/1994 | Murray et al. ................ 156/83 |
| 5,413,788 A | * | 5/1995 | Edwards et al. ............ 424/409 |
| 5,468,738 A | * | 11/1995 | Okabayashi et al. .......... 514/63 |
| 5,478,563 A | * | 12/1995 | Erami ......................... 424/409 |
| 5,503,840 A | * | 4/1996 | Jacobson et al. ............ 424/421 |
| 5,510,109 A | * | 4/1996 | Tomioka et al. ............. 424/421 |
| 5,595,750 A | * | 1/1997 | Jacobson et al. ............ 424/421 |
| 5,714,430 A | * | 2/1998 | Gehrer et al. ................ 502/347 |
| 5,880,044 A | * | 3/1999 | Shimiz ........................ 442/365 |
| 5,929,133 A | * | 7/1999 | Watanabe et al. ............ 523/122 |
| 5,960,578 A | * | 10/1999 | Yasui ............................. 43/23 |
| 6,093,407 A | * | 7/2000 | Cummings et al. .......... 424/400 |
| 2002/0158107 A1 | * | 10/2002 | Yokoo ........................... 228/55 |
| 2003/0031728 A1 | * | 2/2003 | Martin et al. ................ 424/618 |

FOREIGN PATENT DOCUMENTS

KR 2001027619 A * 4/2001 ............ B29C/45/00
KR 2001104010 A * 11/2001 .......... C08L/101/00

OTHER PUBLICATIONS

Obtained translation of KR 2001104010 A (Nov. 24, 2001).*
Obtained translation for KR 2001-027619 A (Apr. 6, 2001), Lee, J. Y.*
Derwent abstract ACC-NO 2002-400869 for KR 2001104010A, Han et al. (Nov. 24, 2001).*
Derwent abstract ACC-NO 2001-587441 for KR 2001027619A, Lee (Apr. 6, 1999).*

* cited by examiner

Primary Examiner—Matthew A. Thexton
(74) Attorney, Agent, or Firm—Squire, Sanders & Dempsey L.L.P.

(57) ABSTRACT

This invention provides a grip for a tool that is treated with an anti-microbial material to minimize germs from passing from one person to another. The anti-microbial material includes: about 90% by weight of feldspar particles; about 5% by weight of alumina whiskers; about 2% by weight of silver; and about 3% by weight of zinc. The grip can be formed for a variety of tools such as a soldering iron.

19 Claims, 3 Drawing Sheets

ANTI-MICROBIAL TOOL GRIP

BACKGROUND OF THE INVENTION

1. Field of the Invention

This invention relates generally to grips or handles for office, industrial or household devices, which have an anti-microbial treatment so that the transfer of germs and bacterium from one handler to another is reduced or eliminated.

2. Description of the Related Art

It is very common for people to share hand held products such as office products, industrial and household tools. This is especially true in manufacturing facilities where multiple workers share the same tools. For instance, in a circuit board fabrication facility, soldering irons for soldering or desoldering components to circuit boards are often shared by workers in subsequent shifts. One of the problems of sharing such tools is that germs and bacterium may pass from the hands of one person to the tool and from the tool to another person. This may lead to workers becoming sick and unable to work, which lowers the productivity of the workers. Therefore, there is a need for reducing the chance of spreading germs through people's hand as they share things such as office or industrial products and tools.

INVENTION SUMMARY

The present invention is directed to grips or handles treated with an anti-microbial material so that the chance of spreading bacterium and germs from one handler to another is minimized. The anti-microbial material may be a composition including: about 85% to about 95% by weight—feldspar (particles); about 2% to about 8.5% by weight—alumina; about 1% to about 4% by weight—silver; and about 2% to about 4% by weight—zinc. The anti-microbial material is selected and formulated to protect against colon *bacillus, pseudomonas aeruginosa, staphylococcus aureus*, molds, and other germs and viruses. As such, this invention protects against bacterium and germs being passed from one handler to another. The anti-microbial material may be a part number AL-F-912AZ manufactured by O.K. Trading Co., LTD.

The above described and many other features and attendant advantages of the present invention will become apparent from a consideration of the following detailed description when considered in conjunction with the accompanying drawings.

DETAILED DESCRIPTION OF THE INVENTION

Figure 1:
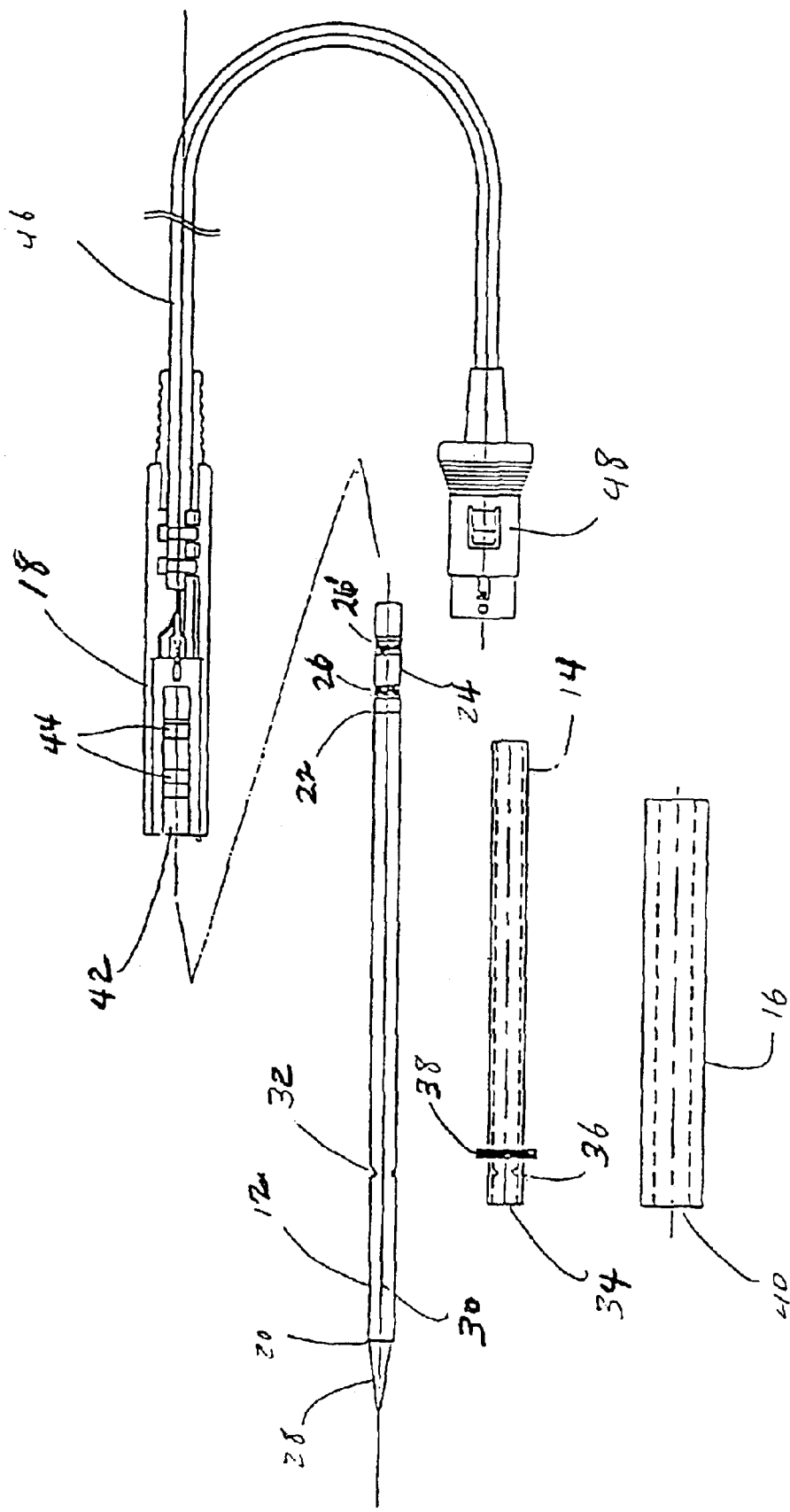
FIG. 1 is a soldering iron with a replaceable handle.
Figure 2:
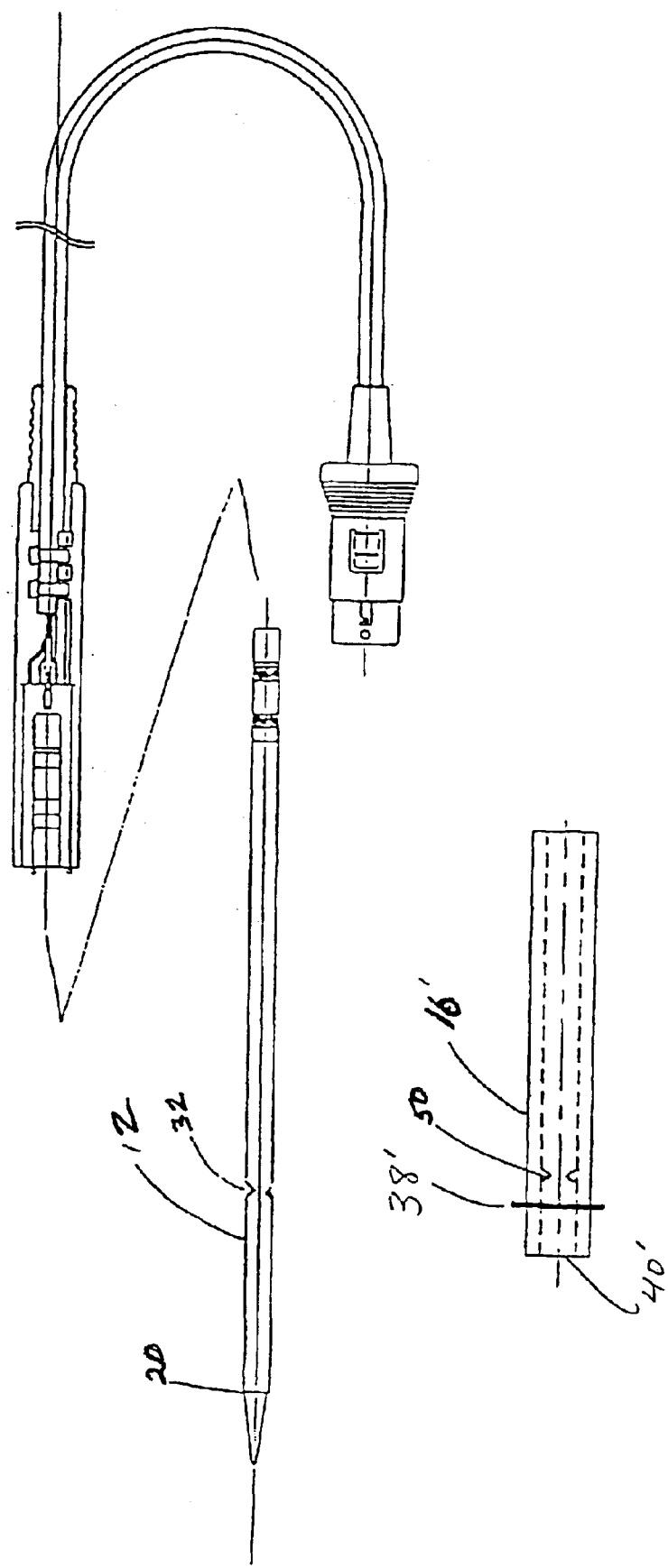
FIG. 2 is another handle for the soldering iron of FIG. 1.
Figure 3:
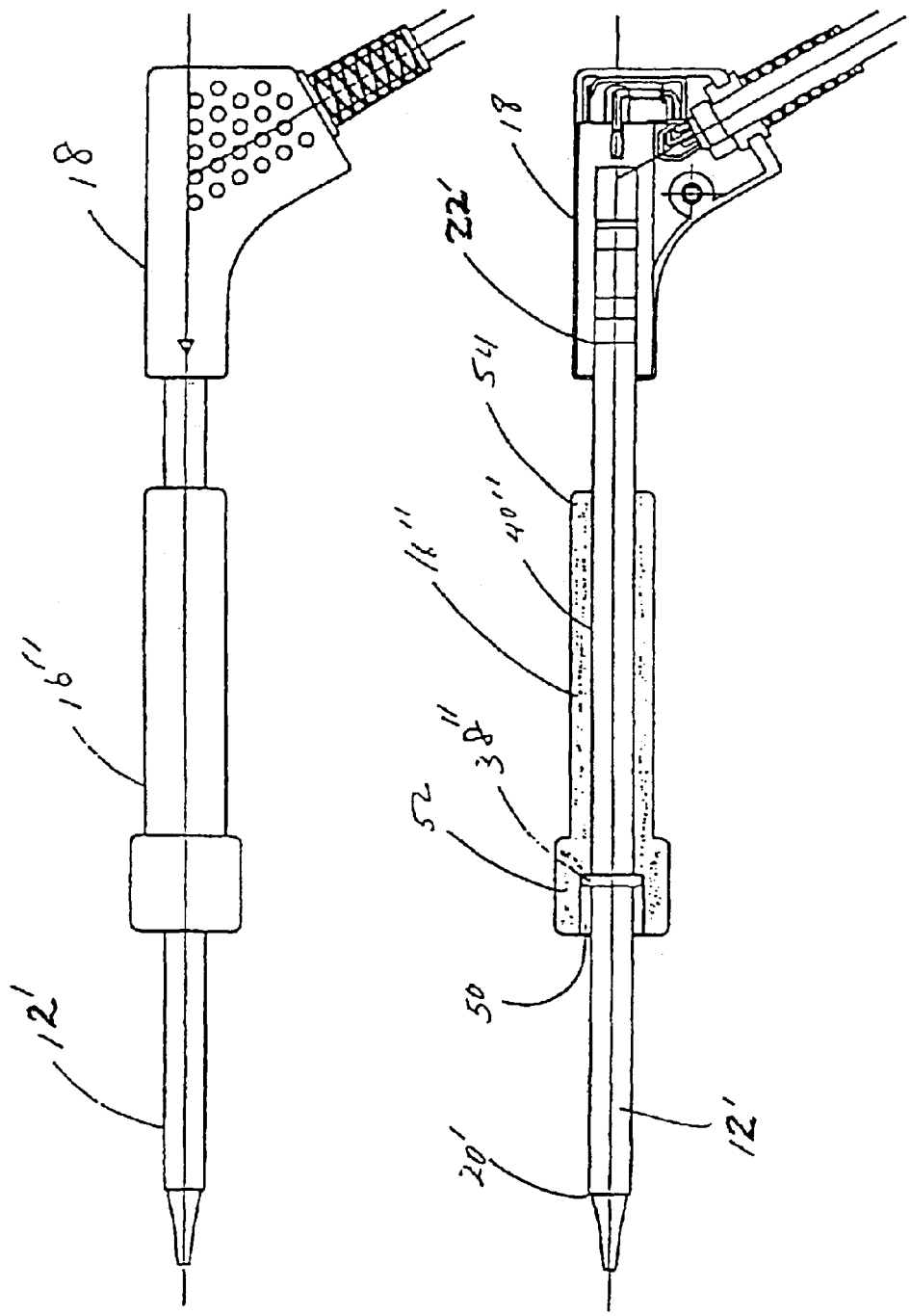
FIG. 3 is still another handle for a soldering iron.

This invention provides a grip or handle that is treated with an anti-microbial material so that chance of spreading bacterium and germs from one handler to another is minimized. The anti-microbial grip may be molded to fit a variety of tools such as a soldering iron. For example, the anti-microbial grip may be molded to form the handle as described in U.S. patent application Ser. No. 09/977,855 ("the '855 Application") entitled A Cartridge Type Soldering Iron with A Releaseable and Replaceable Handle, which is incorporated by reference into this application. FIGS. 1–3 illustrate the handles described in the '855 Application where the handle 16, 16', and 16" may be replaceable. In FIG. 1, the handle 16 may have a hole 40 there through along its longitudinal axis. The configuration of the hole 40 may be substantially similar to the outer configuration of an insulator 14. Once the insulator 14 is inserted into the hole 40, it snugly fits into the hole 40 and it is removable. The outer circumference of the handle 16 may vary in size, shape, and may have different degrees of firmness. This allows a particular user to pick a handle that is ergonomically comfortable to grip. The anti-microbial material incorporated into the handle minimizes the transfer of germs from one user to the next user.

FIG. 2 illustrates that the sleeve 12 may be releasable from the handle 16', and the handle 16' may have a tooth 50 adapted to associate with the notch 32 of the sleeve 12 to position the handle 16' relative to the sleeve 12 at a predetermined position. Put differently, the handle 16 may be replaceable from the soldering iron. FIG. 3 illustrates that the sleeve 12' has a ring 38" at a predetermined position to act as a stopper along a longitudinal axis of the sleeve 12'. As the sleeve is inserted into the hole 40" of the handle 16", the ring 38" acts as a stopper to prevent the handle 16" from moving further toward the distal end 20' of the sleeve 12'. This ensures that the handle 16" is correctly positioned relative to the sleeve 12'. With this invention, different technicians may use the soldering iron without passing germs from their hands to others. This disclosed product is representative of an industrial tool. Of course, those skilled in the art will appreciate that the grip device described herein can be adapted to a wide range of products, such as grips for tools like screw drivers; office products like pens; and home devices like a remote control device.

The anti-microbial material may be a composition including: about 85% to about 95% by weight—feldspar (particles); about 2% to about 8.5% by weight—alumina; about 1% to about 4% by weight—silver; and about 2% to about 4% by weight—zinc. In one embodiment, the anti-microbial material composition may include, by weight percentages: about 90% feldspar; about 5% alumina whiskers: about 2% silver; and about 3% zinc. The feldspar particles may form the core of the anti-microbial material with the alumina whiskers on the feldspar particles. The silver may act as the anti-microbial material that is coated onto the alumina. The zinc may also be coated onto the alumina to protect the silver against UV rays. Similar types of anti-microbial materials may be used. To form the grip, about 5% to about 0.5% by weight of the anti-microbial material may be mixed with plastic material such as vinyl chloride to mold an anti-microbial grip. In particular, about 1% by weight of the anti-microbial material may be mixed with a plastic material and then molded to form an anti-microbial grip.

An anti-microbial grip formed from the foregoing materials has been tested for its effectiveness. In the first test, three types of viruses were tested: (1) *Staphylococcus aureus*; (2) Colon *bacillus*; and (3) *Pseudomonas aeruginosa*, with the inoculated quantity of $1.6 \times 10^5$, $4.2 \times 10^6$, and $1.4 \times 10^6$, respectively. Each virus was inoculated into a test sample in the form of a dip cast in the shape of a plate that was treated with anti-microbial material. A film was put on the test sample to cover the outflow of virus. For comparison, each of the three viruses with the same inoculated quantity was inoculated onto a film without the anti-microbial treatment. After 24 hours of inoculation at 35° C., the following test results were obtained:

|  | Staphylococcus aureus | Colon bacillus | Pseudomonas aeruginosa |
|---|---|---|---|
| Inoculated Qty | $1.6 \times 10^5$ | $4.2 \times 10^6$ | $1.4 \times 10^6$ |
| Sample | none detected | none detected | none detected |
| Film | $6.0 \times 10^5$ | $9.1 \times 10^6$ | $5.0 \times 10^5$ |

In the second test, the test-tube immersing method was used. In this test, two sleeves, sleeve A and sleeve B, both having tubular shapes were tested. The sleeve A was treated with the anti-microbial material, but the sleeve B was not treated. The sleeve A was put into a test tube with culture fluid inoculated with the same viruses as in the first test. The sleeve B was put into another test tube with culture fluid inoculated with the same viruses as in the first test as well. For comparison, culture fluid inoculated with the same viruses without any sleeve was also tested. The shacking cultivation was carried out for 24 hours, and the number of raw virus in the test tubes were measured. The following test results were obtained:

|  | Staphylococcus aureus | Colon bacillus | Pseudomonas aeruginosa |
|---|---|---|---|
| Inoculated Qty | $1.6 \times 10^5$ | $4.2 \times 10^6$ | $1.4 \times 10^6$ |
| Sleeve A | none detected | none detected | none detected |
| Sleeve B | $1.6 \times 10$ | $2.4 \times 10^3$ | $1.7 \times 10^3$ |
| Culture Fluid only | $6.8 \times 10^6$ | $6.6 \times 10^4$ | $6.4 \times 10^3$ |

Based on the test results, both samples substantially reduced the count of the *Staphylococcus*; Colon *bacillus*; and *Pseudomonas aeruginosa* viruses, illustrating that incorporating the anti-microbial material into a sleeve minimizes spreading viruses from one person to another. This helps to keep the work place free of viruses and reduce the chance of workers becoming sick from such viruses.

In closing, it is noted that specific illustrative embodiments of the invention have been disclosed hereinabove. With respect to the claims, it is applicant's intention that the claims not be interpreted in accordance with the sixth paragraph of 35 U.S.C. § 112 unless the term "means" is used following by a functional statement.

What is claimed is:

1. A composition for an anti-microbial grip, comprising:
   about 95% to about 99.5% by weight of a plastic material; and
   about 5% to about 0.5% by weight of anti-microbial material, the plastic material and the anti-microbial material molded to form a grip for a tool handle, where the anti-microbial material includes:
      about 85% to about 95% by weight of feldspar particles;
      about 2% to about 8.5% by weight of alumina whiskers;
      about 1% to about 4% by weight of silver; and
      about 2% to about 4% by weight of zinc.

2. The composition according to claim 1, where the anti-microbial material includes:
   about 90% by weight of feldspar particles;
   about 5% by weight of alumina whiskers;
   about 2% by weight of silver; and
   about 3% by weight of zinc.

3. The composition according to claim 1, wherein the tool handle is a grip for a soldering iron.

4. The composition according to claim 1, where the plastic material is a vinyl chloride.

5. A method for minimizing transfer of germs from a tool, comprising:
   mixing about 5% to about 0.5% by weight of anti-microbial material with about 95% to about 99.5% by weight of a plastic material to form a mixed material, wherein the anti-microbial material includes about 85% to about 95% by weight of feldspar particles, about 2% to about 8.5% by weight of alumina whiskers, about 1% to about 4% by weight of silver; and about 2% to about 4% by weight of zinc;
   forming a grip with the mixing of the anti-microbial material and the plastic material; and
   placing the grip around a tool to form handle so that chance of spreading bacterium and germs from one user to another is minimized.

6. The method according to claim 5, where the tool is a soldering iron.

7. An anti-microbial grip, comprising:
   a soldering iron having a handle; and
   means for treating the handle to minimize spreading germs from one handler to another.

8. The anti-microbial grip according to claim 7, where the means for is an anti-microbial material comprising:
   about 85% to about 95% by weight of feldspar particles;
   about 2% to about 8.5% by weight of alumina whiskers;
   about 1% to about 4% by weight of silver; and
   about 2% to about 4% by weight of zinc.

9. A soldering iron, comprising:
   a soldering iron having a handle having an anti-microbial material, where the handle is comprised of composition including:
      about 85% to about 95% by weight of feldspar particles;
      about 2% to about 8.5% by weight of alumina whiskers;
      about 1% to about 4% by weight of silver; and
      about 2% to about 4% by weight of zinc.

10. The soldering iron according to claim 9, where the feldspar particles is about 90% by weight, the alumina whiskers is about 5% by weight, silver is about 2% by weight, and zinc is about 3% by weight.

11. The soldering iron according to claim 9, where the handle is replaceable.

12. The soldering iron according to claim 9, where the handle is formed from:
   about 95% to about 99.5% by weight of a plastic material; and
   about 5% to about 0.5% by weight of anti-microbial material.

13. A method for minimizing transfer of germs from a soldering iron, comprising:
   means for treating the handle of the soldering iron with anti-microbial material.

14. The method according to claim 13, wherein the treating comprises:
   covering the handle with a replaceable anti-microbial sleeve.

15. The method according to claim 13, wherein the treating comprises:
   mixing about 5% to about 0.5% by weight of the anti-microbial material with about 95% to about 99.5% by weight of a plastic material to form a mixed material;
   forming a grip with the mixing of the anti-microbial material and the plastic material; and placing the grip around the handle so that chance of spreading bacterium and germs from one user to another is minimized.

16. A composition for an anti-microbial grip, comprising:

about 95% to about 99.5% by weight of a plastic material; and about 5% to about 0.5% by weight of anti-microbial material, wherein the anti-microbial material includes about 85% to about 95% by weight of feldspar particles, about 2% to about 8.5% by weight of alumina whiskers, about 1% to about 4% by weight of silver; and about 2% to about 4% by weight of zinc.

17. A composition for an anti-microbial grip, comprising:

about 95% to about 99.5% by weight of a plastic material; and about 5% to about 0.5% by weight of anti-microbial material, wherein the anti-microbial material includes about 90% by weight of feldspar particles, about 5% by weight of alumina whiskers, about 2% by weight of silver; and about 3% by weight of zinc.

18. An anti-microbial grip, comprising:

a soldering iron having a handle; and means for treating the handle to minimize spreading germs from one handler to another, wherein the means for is an anti-microbial material comprising about 85% to about 95% by weight of feldspar particles, about 2% to about 8.5% by weight of alumina whiskers, about 1% to about 4% by weight of silver; and about 2% to about 4% by weight of zinc.

19. An anti-bacterial grip, comprising:

a soldering iron having a handle; and means for treating the handle to minimize spreading germs from one handler to another, wherein the means for is an anti-microbial material comprising about 85% to about 95% by weight of feldspar particles, about 2% to about 8.5% by weight of alumina whiskers, about 1% to about 4% by weight of silver; and about 2% to about 4% by weight of zinc.

* * * * *